(12) United States Patent
Dixon, Jr. et al.

(10) Patent No.: US 6,863,882 B2
(45) Date of Patent: Mar. 8, 2005

(54) STABLE ORAL COMPOSITIONS COMPRISING CASEIN PHOSPHOPEPTIDE COMPLEXES AND FLUORIDE

(75) Inventors: Cloyd Dixon, Jr., Covington, KY (US); Michael Anthony Kaminski, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/320,871

(22) Filed: Dec. 17, 2002

(65) Prior Publication Data

US 2003/0124066 A1 Jul. 3, 2003

Related U.S. Application Data

(60) Provisional application No. 60/345,916, filed on Jan. 3, 2002.

(51) Int. Cl.[7] .................................................. A61K 7/18
(52) U.S. Cl. ......................................................... 424/52
(58) Field of Search ...................................... 424/50, 52

(56) References Cited

U.S. PATENT DOCUMENTS

| | | | |
|---|---|---|---|
| 4,460,565 A | * | 7/1984 | Weststrate et al. ............ 424/52 |
| 4,601,899 A | | 7/1986 | Stier et al. |
| 5,015,628 A | | 5/1991 | Reynolds |
| 5,227,154 A | | 7/1993 | Reynolds |
| 5,578,294 A | * | 11/1996 | Lukacovic .................... 424/52 |
| 5,834,427 A | | 11/1998 | Han et al. |
| 5,981,475 A | | 11/1999 | Reynolds |
| 6,013,274 A | * | 1/2000 | Chaykin ...................... 424/440 |
| 2003/0007937 A1 | * | 1/2003 | Lawlor ........................ 424/57 |

FOREIGN PATENT DOCUMENTS

| | | |
|---|---|---|
| AU | 721548 B3 | 1/2000 |
| EP | 166055 | 1/1986 |
| EP | 344832 | 6/1989 |
| EP | 342380 | 11/1989 |
| EP | 528458 A1 | 3/1992 |
| EP | 523776 | 1/1993 |
| JP | 4077415 | 11/1992 |
| JP | 09/175971 | 8/1997 |
| JP | 2960176 B1 | 10/1999 |
| WO | WO 94/00146 | 1/1994 |
| WO | WO 98/40406 | 9/1998 |
| WO | WO 00/06108 | 2/2000 |

* cited by examiner

*Primary Examiner*—Raymond J. Henley, III
(74) *Attorney, Agent, or Firm*—Betty J. Zea

(57) ABSTRACT

The present invention relates to oral care compositions, especially toothpastes, comprising: a safe and effective amount of phosphopeptide-amorphous calcium phosphate complex ("PP-ACP"); a safe and effective amount of a fluoride ion source; a pharmaceutically-acceptable topical, oral carrier, and a safe and effective amount of a calcium chelator, wherein the composition has improved fluoride stability. This invention further relates to a method of maintaining the fluoride levels in an oral care composition comprising a safe and effective amount of PP-ACP, a safe and effective amount of a fluoride ion source, and a pharmaceutically-acceptable topical, oral carrier, by adding, to the composition, a safe and effective amount of a calcium chelator.

13 Claims, No Drawings

STABLE ORAL COMPOSITIONS COMPRISING CASEIN PHOSPHOPEPTIDE COMPLEXES AND FLUORIDE

CROSS REFERENCE TO RELATED APPLICATIONS

This application claims the benefit of U.S. Provisional Application No. 60/345,916 filed Jan. 3, 2002.

TECHNICAL FIELD

The present invention relates to oral care compositions comprising complexes of amorphous calcium phosphate and phosphopeptides, a fluoride ion source, and a calcium chelator, wherein the composition has enhanced fluoride stability.

BACKGROUND ART

In the mouth a natural equilibrium exists between hydroxyapatitie being dissolved from the enamel of teeth, on the one hand, and hydroxyapatitie being formed on or in the teeth from substances occurring naturally in the saliva, on the other hand. When the equilibrium is such that the hydroxyapatite is dissolved, a cariogenic condition arises which is referred to as demineralization. If the equilibrium is such that hydroxyapatite is being formed in demineralized enamel, this is referred to as remineralization. By remineralization, pre-existing tooth decay and caries can be reduced or eliminated by natural means.

It has long been known that fluoride-providing compounds, even in low concentrations, are a safe and effective means for the promotion of the remineralization process. In addition the prior art, specifically WO 98/40406, published Sep. 17, 1998, The University of Melbourne and The Victorian Dairy Industry Authority, Reynolds, teaches phosphopeptides (casein derived or otherwise) containing the cluster sequence motif Ser(P)-Ser(P)-Ser(P)-Glu-Glu- (herein referred to as "PP") can stabilize their own weight in amorphous calcium phosphate (herein referred to as "ACP"). The amorphous phases stabilized by the phosphopeptides are taught as an excellent delivery vehicle to co-localize Ca, F, and phosphate at the tooth surface in a slow-release amorphous form producing good anticaries efficacy.

Despite the above known prior art and technologies for treatment of caries, the prior art has not fully appreciated or solved problems associated with combining PP-ACP with other ingredients to form oral care, composition such as dentifrices or mouthrinses. In particular, certain incompatibilities may arise with respect to the addition of PP-ACP with other components such as fluoride, rendering reduced fluoride ions levels within the oral care formulation. The present invention minimizes this instability of the combination of fluoride ions and PP-ACP through the addition of a calcium chelator at specific levels.

SUMMARY OF THE INVENTION

The present invention relates to oral care compositions, including therapeutic rinses, especially mouth rinses, as well as toothpastes or dentifrices, tooth gels, tooth powders, non-abrasive gels, and mouth sprays, comprising:
(a) a safe and effective amount of phosphopeptide-amorphous calcium phosphate complex (herein "PP-ACP");
(b) a safe and effective amount of a fluoride ion source;
(c) a safe and effective amount of a calcium chelator; in another embodiment the calcium chelator is selected from the group consisting of tartaric acid and salts thereof, citric acid and salts thereof, pyrophosphate ion source, polyphosphate, diphosphonates, and mixtures thereof;
(d) pharmaceutically-acceptable topical, oral carrier; wherein the level of fluoride ion is maintained.

This invention further relates to a method of maintaining fluoride levels in an oral care composition comprising a safe and effective amount of PP-ACP, a safe and effective amount of a fluoride ion source, and a pharmaceutically-acceptable topical, oral carrier, by adding, to the composition, a safe and effective amount of a calcium chelator.

All levels herein are by weight of the composition unless otherwise indicated.

DETAILED DESCRIPTION OF THE INVENTION

The present invention relates to oral care compositions, including therapeutic rinses, especially mouth rinses, as well as toothpastes or dentifrices, tooth gels, tooth powders, non-abrasive gels, and mouth sprays, comprising:
(a) a safe and effective amount of PP-ACP, in another embodiment at a level of from about 0.01% to about 25%, in another embodiment at a level of from about 0.1% to about 10%; in even another embodiment at a level of from about 0.2% to about 2%, by weight of the composition;
(b) a safe and effective amount of a fluoride ion source, in another embodiment at a level of from about 50 ppm to about 3500 ppm, in even another embodiment at a level of from about 200 ppm to about 3000 ppm; in yet another embodiment at a level of from about 500 ppm to about 2,800 ppm; and in even another embodiment from about 850 ppm to about 1,100 ppm;
(c) a safe and effective amount of a calcium chelator; in another embodiment the calcium chelator is at a level of from about 0.001% to about 20%, by weight of the composition; in another embodiment the calcium chelator is selected from the group consisting of tartaric acid and salts thereof, citric acid and salts thereof, pyrophosphate ion source, polyphosphate, diphosphonates, and mixtures thereof; in another embodiment the calcium chelator is a pyrophosphates ion source;
(d) pharmaceutically-acceptable topical, oral carrier; wherein the fluoride ion levels are maintained.

This invention further relates to a method of maintaining fluoride levels in an oral care composition comprising a safe and effective amount of PP-ACP, a safe and effective amount of a fluoride ion source, and a pharmaceutically-acceptable topical, oral carrier, by adding, to the composition, a safe and effective amount of a calcium chelator.

By "safe and effective amount" as used herein is meant an amount of a component, high enough to significantly (positively) modify the condition to be treated or to effect the desired anticaries result, but low enough to avoid serious side effects (at a reasonable benefit/risk ratio), within the scope of sound medical/dental judgment. The safe and effective amount of a component, will vary with the particular condition (e.g., to effect anticaries activity or remineralization effect) being treated, the age and physical condition of the patient being treated, the severity of the condition, the duration of treatment, the nature of concurrent therapy, the specific form employed, and the particular vehicle from which the component is applied.

By "toothpaste" as used herein is meant paste, powder, and tooth gel formulations unless otherwise specified.

By "oral care composition" or "oral composition" as used herein is meant a product which is not intentionally swallowed for purposes of systemic administration of therapeutic agents, but is retained in the oral cavity for a sufficient time to contact substantially all of the dental surfaces and/or oral mucosal tissues for purposes of oral activity.

By "maintaining fluoride levels" as used herein is meant that the levels of fluoride in the oral care composition do not significantly decrease over time. First, the level of soluble fluoride is measured on a sample of fresh product. Fresh product samples are those prepared and analyzed within 14 days of preparation. Thereafter the level of fluoride is measured on aged product, defined as product at the effective end of their expiration period which can be any period of time, e.g. 1 month, 2 months, etc. up to about 1–2 years. Samples can be aged either under normal, ambient, representative conditions, or by high temperature (e.g. 40 C.), accelerated aging. The methodology, pH and dilution conditions must be consistent for measurements on both aged and fresh samples. The method generally involves the preparation of a standard solution for calibration of the fluoride electrode, preparation of the fluoride electrode and calibration curve, preparation of the product sample usually with a buffer, and calculation of the product fluoride concentration. The levels of fluoride can be measured via any known test method for measuring fluoride, including methods outlined in 21 CFR Ch. 1(4-1-01 ed.) Pt. 355 for anticaries drug products for OTC use and methods established by the American Dental Association in the *ADA Acceptance Program Guidelines for Fluorid-Containing Dentifrices* relating to fluoride availability and stability, May 1998, both of which are herein incorporated by reference.

For compositions of the present invention the level of fluoride for stored (aged) product is no more than about 20% lower than the level of fluoride in the fresh product; in another embodiment the level of fluoride of aged product is no more than about 15% lower, in yet another embodiment no more than 10% lower, in yet another embodiment no more than 5% lower than the level for fresh product. In another embodiment the fluoride level of aged product is only from about 1% to about 20% lower than the level of fluoride for fresh product; in another embodiment the fluoride level of aged product is only from about 2.5% to about 15%, or from about 5% to about 10% lower than the level of fluoride of fresh product.

PP-ACP

The PP-ACP is a stable calcium phosphate complex, comprising amorphous calcium phosphate (ACP) or a derivative thereof, stablized by a phosphopeptide, wherein said phosphopeptide comprises the sequence Ser(P)-Ser(P)-Ser(P)-Glu-Glu- (herein called "Ser(P) cluster sequence motif". The amorphous calcium phospate (ACP) is preferably of the formula $[Ca_3(PO_4)_{1.87}(HPO_4)_{0.2}xH_2O]$ wherein $x \geq 1$. The Ser(P) cluster sequence motif has the ability to stabilize its own weight in ACP, as taught in WO 98/40406, published, Sep. 17, 1998, The University of Melbourne, the Victorian Dairy Industry Authority, Reynolds, which is herein incorporated by reference in its entirety.

The phosphopeptides of the present invention are preferably in substantially pure form. The phosphopeptide may be made synthetically by chemical synthesis or genetic engineering or can be extracted from naturally occurring materials. For example, the phosphopeptide (PP) may be from any source; it may be obtained by hydrolyzing or digesting (either chemical or proteolytic) a protein or by tryptic digestion of casein or other phospho-acid rich proteins such as phosphitin, or by chemical or recombinant synthesis, provided that it comprises the core sequence -Ser(P)-Ser(P)-Ser(P)-Glu-Glu-. It is preferred to digest casein with trypsin, pepsin, chymotrypsin, papain, thermolysin or pronase, preferably trypsin. It is currently more economic to extract the phosphopeptide from casein and in particular from alpha-s casein or beta-casein. Further, phosphoproteins in cereals, nuts and vegetables particularly in bran husks or sheaths (rice, wheat, oat, barley or rye brans) may be used to produce the peptide above. Soybean and meat contain phosphoproteins which may be of use in obtaining the peptide above. U.S. Pat. No. 5,834,427, issued Nov. 10, 1998, Han et al., assigned to Sang Kee Han, also discloses methods of making phosphopeptides and casein phosphopeptides. This reference is herein incorporated by reference in its entirety.

U.S. Pat. No. 5,015,628, issued May 14, 1991, The University of Melbourne; Victorian Dairy Industry Authority, Reynolds, discloses phosphopeptides which are particularly useful in the present invention. This patent is herein incorporated by reference in its entirety. The sequence flanking this core sequence -Ser(P)-Ser(P)-Ser(P)-Glu-Glu- may be any sequence. However, those flanking sequences disclosed in U.S. Pat. No. 5,015,628, such as $\alpha_{s1}(59-79)$[1] as $\beta(1-25)$ [2], $\alpha_{s2}(46-70)$ [3] and $\alpha_{s2}(1-21)$ [4] are preferred. In particular, preferred phosphopeptides include Bos $\alpha_{s1}$-casin X-5P (f59–79) [1], Bos β-casein X-4P (f1–25) [2], Bos $\alpha_{s2}$-casein X-4P (f46–70) [3] and Bos $\alpha_{s2}$-casein X-4P (f1–21) [4], disclosed in U.S. Pat. No. 5,015,628 as follows:

[1] $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$. $\alpha_{s1}(59-79)$ $(T_1)$

[2] $Arg^1$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$. $\beta(1-25)$ $(T_2)$

[3] $Asn^{46}$-Ala-Asn-Glu-Glu-Glu-Tyr-Ser-Ile-Gly-Ser(P)-Ser(P)-Ser(P)-Glu-Glu -Ser(P)-Ala-Glu-Val-Ala-Thr-Glu-Glu-Val-$Lys^{70}$. $\alpha_{s2}(46-70)$ $(T_4)$

[4] $Lys^1$-Asn-Thr-Met-Glu-His-Val-Ser(P)-Ser(P)-Ser(P)-Glu-Glu-Ser-Ile-Ile-Ser(P)-Gln-Glu-Thr-Tyr-$Lys^{21}$. $\alpha_{s2}(1-21)$ $(T_3)$ The flanking sequences may optionally be modified by deletion, addition or conservative substitution of one or more residues. The amino acid composition and sequence of the flanking region are not critical as long as the conformation of the peptide is maintained and that all phosphoryl and carboxyl groups interacting with calcium ions are maintained as the preferred flanking regions appear to contribute to the structural action of the Ser(P) cluster sequence motif. In one embodiment the PP has less than about 120 amino acid residues, in another embodiment the PP has less than about 100 amino acid residues.

WO 98/40406 teaches an amorphous form of calcium phosphate $Ca_3(PO_4)_{1.87}(HPO_4)_{0.2}xH_2O$ where $x \geq 1$ stablized by the casein phosphopeptides, as a very soluble, basic form of non-crystalline calcium phosphate and a superior form of calcium phosphate which prevents caries and increases calcium bioavailablity. Furthermore, WO 98/40406, further teaches that PP-ACP must be formed by careful titration of calcium ions (e.g. $CaCl_2$) and phosphate ions (e.g. Na HPO4) while maintaining the pH above 7 (preferably 9.0) in the presence of the phosphopeptide. As the ACP is formed, the phosphopeptide binds to the nascent nuclei and stabilizes the ACP as a phosphopeptide-ACP complex. Without the phosphopeptide, the ACP will precipitate out of solution and transform within minutes into the most stable calcium phosphate phase, crystalline hydroxyapatite (HA). HA, by being insoluble has limited anticariogenic activity and presents calcium in a poorly bioavailable form. The acidic phase of calcium phosphate $CaHPO_4$ while certainly being more soluble than hydroxyapatite, is poorly bound by the phosphopeptide and poorly localized at the tooth surface and therefore also has limited anticariogenic activity. The aforementioned phosphopeptides and in particular Ser(P) cluster sequence motif uniquely stabilizes amorphous calcium phosphate to provide a reliable and effective method of producing a stabilized amorphous calcium phosphate complex.

The complex formed preferably has the formula $[(PP)(CP)_8]_n$, where n is equal to or greater than 1, for example, 6. The complex formed may be a colloidal complex.

The phosphopeptide binds to the ACP cluster to produce a metastable solution in which growth of ACP to a size that initiates nucleation and precipitation is prevented. In this way, calcium and other ions such as fluoride ions can be localized, for instance at a surface on a tooth to prevent demineralisation and prevent formation of dental caries.

In a preferred embodiment, the complex is PP-ACP in a slow release amorphous form that produces good anti-caries efficacy. The oral formulations of the present invention may comprise about 0.05 to about 50% by weight of the composition, preferably from about 1.0% to about 15% of CPA-ACP. The oral composition of this invention which contains the above-mentioned agents may be prepared and used in various oral care compositions, including therapeutic rinses, especially mouth rinses, as well as toothpastes or dentifrices, tooth gels, tooth powders, non-abrasive gels, and mouth sprays.

As disclosed in '406 above, producing a stable complex of calcium phosphate, comprises the step of:
(i) obtaining a solution of phosphopeptide having a pH of about 9.0;
(ii) admixing (i) with solutions comprising calcium, and inorganic phosphate at a pH of about 9.0;
(iii) filtering the mixture resulting from step (ii), and
(iv) drying to obtain the said complex the said complex.

As specifically disclosed in '406, PP-ACP can be prepared as follows: a 10% w/v casein (Murray Goulburn, Victoria, Australia) or caseinate solution is prepared at pH 8.0 and then digested with trypsin at 0.2% w/w of the casein for 2 h at 50° C. with the pH controlled to 8.0±0.1 by NaOH addition. After digestion the solution is adjusted to pH 4.6 by the addition of HCl and the precipitate is removed by centrifugation or microfiltration. The solution can also be clarified by microfiltration at pH 8.0 without acidification. The supernatant or microfiltrate is then adjusted to pH 9.0 with NaOH, then $CaCl_2$ (1.6 M) and $Na_2HPO_4$ (1 M) at pH 9.0 are added slowly ($\leq$1% vol per min) with constant agitation with the pH held constant at 9.0±0.1 by NaOH addition. $CaCl_2$ and sodium phosphate are added to the final concentrations of 100 mM and 60 mM respectively. Following the addition of the calcium and phosphate solutions, the solution is microfiltered through a 0.1 or 0.2 µm microfilter (ceramice or organic) to concentrate the solution five fold. The retentate is then diafiltered with one to five volumes of casein PP and 40% ACP and residue water. As indicated in '406, analysis of CPP of the PP-ACP complex by reversed-phase HPLC, sequence analysis and mass spectrometry revealed that the only peptides that are capable of stabilizing the amorphous calcium phosphate and retained during the microfiltration and diafiltration are Bos $\alpha_{s1}$-casein X-5P (f59–79) [1,] Bos β-casein X-4P (f1–25) [2], Bos $\alpha_{s2}$-casein X-4P (f46–70) [3] and Bos $\alpha_{s2}$-casein X-4P (f1–21) [4] and truncated and heat modified forms of these peptides.

Casein phosphopeptides containing the Ser(P) cluster sequence motif have a marked ability to stabilize calcium phosphate in solution. Solutions containing 0.1% w/v $\alpha_{s1}$ (59–79) [1] at various pH, calcium and phosphate concentrations, but constant ionic strengths can be used to characterize the peptide's interaction with calcium phosphate. The peptide has been found to maximally bind 24 calcium and 16 phosphate per molecule as discussed in '406.

The '406 reference teaches that $[Ca_3(PO_4)_{1.87}(HPO_4)_{0.2} xH_2O]$ is the ACP phase stabilized by $\alpha_{s1}$(59–79). The peptide (PP) binds to forming ACP clusters producing a metastable solution preventing ACP growth to the critical size required for nucleation and precipitation. For example, as taught in '406 the binding of $\alpha_{s1}$(59–79) to ACP results in the formation of colloidal complexes with the unit formula $[\alpha_{s1}(59-79)(ACP)_8]n$ where n is equal to or greater than one. It is likely that the predominant form is n=6 as $\alpha_{s1}$(59-79) cross-linked with glutaraldehyde in the presence of ACP runs as a hexamer on polyacrylamide gel electrophoresis.

The concentration of PP-ACP in the composition of the present invention depends on the type of composition (e.g., toothpaste, mouthrinse, etc) used to apply it to the gingival/mucosal tissue and/or the teeth, due to possible differences in efficiency of the compositions contacting the tissue and teeth, and also due to the amount of the composition generally used. The concentration may also depend on the degree of disease or condition being treated.

In one embodiment the mouth rinse or mouth sprays to be taken into the oral cavity have a concentration of PP-ACP in the range of from about 0.01% to about 20%, in another embodiment from about 0.04% to about 4%, with from about 0.075% to about 3% in another embodiment and from about 0.5% to about 2.5%, by weight of the composition, in even another embodiment.

For dentifrices (including toothpaste and tooth gels) and non-abrasive gels, the concentration of PP-ACP is in the range of from about 0.01% to about 20%, in another embodiment from about 0.1% to about 10%, by weight of the composition, with from about 0.75% to about 5% in another embodiment, and from about 0.2% to about 2.5% by weight of the composition, in yet another embodiment.

Fluoride Ion Source

The present invention also includes a fluoride ion source, with free fluoride ions. In one embodiment the free fluoride ions can be provided by sodium fluoride, stannous fluoride, indium fluoride, and sodium monofluorophosphate. Sodium fluoride is the free fluoride ion in another embodiment. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, in another embodiment from about 200 ppm to about 3000 ppm, and in another embodiment from about 500 ppm to about 2,800 ppm, and in even another embodiment from about 850 ppm to about 1,100 ppm, of free fluoride ions.

Calcium Chelating Agent

The compositions and methods of the present invention comprise a safe and effective amount of a calcium chelator; in another embodiment the calcium chelator is from about 0.001% to about 20%, and in another embodiment is less than about 5%, in another embodiment is from about 0.1% to about 5%, in even another embodiment is from about 0.5% to about 3%, by weight of the composition.

Suitable calcium chelators for use in the present invention are selected from the group consisting of tartaric acid and pharmaceutically acceptable salts thereof; citric acid and salts thereof such as alkali metal citrates; pyrophosphate ion source; polyphosphates (e.g., tripolyphosphate, hexametaphosphate); diphosphonates (e.g., EHDP; AHP); and mixtures thereof.

In another embodiment the calcium chelator is selected from the group consisting of sodium citrate, potassium citrate, disodium tartrate, dipotassium tartrate, pyrophosphate ion source, sodium potassium tartrate, disodium hydrogen tartrate, potassium hydrogen tartrate, disodium dihydrogen pyrophosphate, tetrasodium pyrophosphate, tetrapotassium pyrophosphate, and mixtures thereof.

Pyrophosphate/Polyphosphate

A polyphosphate is generally understood to consist of two or more phosphate molecules arranged primarily in a linear configuration, including pyrophosphate and tripolyphosphate, although some cyclic derivatives may be present. Polyphosphates larger than tetrapolyphosphate usually occur as amorphous glassy materials. Included in this invention are the linear "glassy" polyphosphates having the formula:

wherein X is sodium, potassium, or hydrogen and n averages from about 6 to about 125. For example, polyphosphates are manufactured by FMC Corporation which are commercially known as Sodaphos (n≈6), Hexaphos (n≈13), and Glass H (n≈21). In one embodiment Hexaphos and Glass H are the calcium chelators in the composition of this invention. Polyphosphates may be used alone or in combination.

The pyrophosphate ion source is generally from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 0.1% to about 20%, in another embodiment from about 1% to about 10%, and in another embodiment from about 1.5% to about 5% by weight. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1% to about 15%, in another embodiment from about 1.5% to about 10%, and in even another embodiment from about 1.5% to about 5%, by weight of the composition.

Compositions may also comprise a mixture of dissolved and undissolved pyrophosphate salts. Any of the above mentioned pyrophosphate salts may be used.

The phosphate sources and pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

The pH of the final composition is generally from about 5 to about 12, in another embodiment the pH is from about 6 to about 10, in another embodiment the pH is from about 6.5 to about 9. The pH is measured by known methodology for measuring pH of a dentifrice or mouthrinse formulation, using pH electrode with known pH standards.

Topical, Oral Carrier

By "pharmaceutically-acceptable topical oral carrier," or "topical, oral carrier" as used herein, is meant one or more compatible solid or liquid filler diluents or encapsulating substances which are suitable for topical, oral administration. By "compatible," as used herein, is meant that the components of the composition are capable of being commingled without interaction in a manner which would substantially reduce the composition's stability and/or efficacy for treating or preventing oral care conditions such as caries, according to the compositions and methods of the present invention.

The carriers of the present invention may include the usual and conventional components of toothpastes (including gels and gels for subgingival application), mouth rinses, mouth sprays, as more fully described hereinafter.

The choice of a carrier to be used is basically determined by the way the composition is to be introduced into the oral cavity. If a tooth paste (including tooth gels, etc.) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos. 5,198,220, Damani, issued Mar. 30, 1993, P&G, 5,242, 910, Damani, issued Sep. 7, 1993, P&G, all of which are incorporated herein by reference. Carriers suitable for the preparation of compositions of the present invention are well known in the art. Their selection will depend on secondary considerations like taste, cost, and shelf stability, etc.

Preferred compositions of the subject invention are in the form of dentifrices, such as toothpastes, tooth gels and tooth powders. Components of such toothpaste and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an additional anticaries agent (from about 0.05% to about 10% additional anticaries agent), and an anticalculus agent (from about 0.1% to about 13%). Tooth powders, of course, contain substantially all non-liquid components.

Other preferred compositions of the present invention are non-abrasive gels, including subgingival gels, which generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), water (from about 2% to about 45%), and may comprise an additional anticaries agent (from about 0.05% to about 10% of additional anticaries agent), and an anticalculus agent (from about 0.1% to about 13%).

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an of additional anticaries agent (from about 0.05% to about of additional anticaries agent), and an anticalculus agent (from about 0.1% to about 13%).

Other preferred compositions of the subject invention are dental solutions. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Types of carriers which may be included in compositions of the present invention, along with specific non-limiting examples, are:

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference in their entirety. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail in Wason, U.S. Pat. No. 4,340,583, issued Jul. 29, 1982. The abrasive in the toothpaste compositions described herein is generally present at a level of from about 6% to about 70% by weight of the composition. Preferably, toothpastes contain from about 10% to about 50% of abrasive, by weight of the composition.

A particularly preferred precipitated silica is the silica disclosed in U.S. Pat. Nos. 5,603,920, issued on Feb. 18, 1997; 5,589,160, issued Dec. 31, 1996; 5,658,553, issued Aug. 19, 1997; 5,651,958, issued Jul. 29, 1997, all of which are assigned to the Procter & Gamble Co. All of these patents are incorporated herein by reference in their entirety.

Mixtures of abrasives can be used. All of the above patents regarding dental abrasives are incorporated herein by reference. The total amount of abrasive in dentifrice compositions of the subject invention generally range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. No. 3,988,433 to Benedict; U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a.) Nonionic and Amphoteric Surfactants

Nonionic surfactants which may be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention may be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, in another embodiment from about 0.05% to about 4%, and in even another embodiment from about 0.1% to about 3% by weight.

b.) Anionic Surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition may typically comprise an anionic surfactant at a level of from about 0.025% to about 9%, in another embodiment from about 0.05% to about 7%, and in even another embodiment from about 0.1% to about 5% by weight.

Thickening Agents

In preparing toothpaste or gels, it is necessary to add some thickening material to provide a desirable consistency of the composition, to provide desirable release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Thickening agents can include however, except polymeric polyether compounds, e.g., polyethylene or polypropylene oxide (M.W. 300 to 1,000,000), capped with alkyl or acyl groups containing 1 to about 18 carbon atoms.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220, Damani, issued Mar. 30, 1993, P&G, 5,242,910, Damani, issued Sep. 7, 1993, P&G, and 4,443,430, Mattei, issued Apr. 17, 1984, all of which are incorporated herein by reference.

Thickening agents in an amount from about 0.1% to about 15%, or from about 0.2% to about 6%, in another embodiment from about 0.4% to about 5%, by weight of the total toothpaste or gel composition, can be used. Higher concentrations can be used for sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents may also be added to the compositions. Suitable flavoring agents include oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, in another embodiment from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, in another embodiment from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984 WS-3 and other agents are described in U.S. Pat. No. 4,136,163, Watson, et al., issued Jan. 23, 1979; the disclosure of both are herein incorporated by reference in their entirety.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Anticalculus Agent

If the calcium chelator is not a pyrophosphate or polyphosphate, then optionally the compositions of the present invention can include pyrophosphate or polyphosphate as an anticalculus agent such as those described above.

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and in another embodiment from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Antimicrobial antiplaque agents may also by optionally present in oral compositions. Such agents may include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251, 591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above antimicrobial antiplaque agents. If present, the antimicrobial antiplaque agents generally comprise from about 0.1% to about 5% by weight of the compositions of the present invention.

Anti-inflammatory agents may also be present in the oral compositions of the present invention. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenarmic acid, and mixtures thereof. If present, the anti-inflammatory agents generally comprise from about 0.001% to about 5% by weight of the compositions of the present invention. Ketorolac is described in U.S. Pat. No. 5,626,838, issued May 6, 1997, incorporated herein by reference in its entirety.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152,420 to Gaffar, U.S. Pat. No. 3,956,480 to Dichter et al., U.S. Pat. No. 4,138,477 to Gaffar, U.S. Pat. No. 4,183, 914 to Gaffar et al., and U.S. Pat. No. 4,906,456 to Gaffar et al., all of which are incorporated herein by reference in their entirety. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

The present invention may also optionally comprise selective H-2 antagonists including compounds disclosed in U.S. Pat. No. 5,294,433, Singer et al., issued Mar. 15, 1994, which is herein incorporated by reference in its entirety.

Composition Use

The present invention also relates to a method of recrystallizing and/or remineralising enamel and/or dentine in humans or lower animals in need thereof, by administering an effective amount of the compositions of the present invention described above, to the oral cavity by application methods described below.

A safe and effective amount of the compositions of the present invention may be topically applied to the mucosal tissue of the oral cavity, to the gingival tissue of the oral cavity, and/or to the surface of the teeth, for the treatment or prevention of the above mentioned conditions of the oral cavity, in several conventional ways. For example, the gingival or mucosal tissue may be rinsed with a solution (e.g., mouth rinse, mouth spray); or in a dentifrice (e.g., toothpaste, tooth gel or tooth powder), the gingival/mucosal tissue and/or teeth are bathed in the liquid and/or lather generated by brushing the teeth. Other non-limiting examples include applying a non-abrasive gel or paste, directly to the gingival/mucosal tissue or to the teeth with or without an oral care appliance described below. Preferred methods of using the compositions of this invention are via rinsing with a mouth rinse solution and via brushing with a dentifrice.

For the method of treating diseases or conditions of the oral cavity, including caries, a safe and effective amount of the present compositions are preferably applied to the gingival/mucosal tissue and/or the teeth (for example, by rinsing with a mouthrinse, directly applying a non-abrasive gel with or without a device, applying a dentifrice or a tooth gel with a toothbrush, etc.) preferably for at least about 10 seconds, in another embodiment from about 20 seconds to about 10 minutes, in even another embodiment from about 30 seconds to about 60 seconds. The method often involves expectoration of most of the composition following such contact. The frequency of such contact is preferably from about once per week to about four times per day, in another embodiment from about thrice per week to about three times per day, in even another embodiment from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity. The period of such treatment typically ranges from about one day to a lifetime. The subject may repeat the application as needed. The duration of treatment is preferably from about 3 weeks to about 3 months, but may be shorter or longer depending on the severity of the condition being treated, the particular delivery form utilized and the patient's response to treatment.

The compositions of this invention are useful for both human and other lower animal (e.g. pets, zoo, or domestic animals) applications.

The following non-limiting examples further describe preferred embodiments within the scope of the present invention. Many variations of these examples are possible without departing from the scope of the invention.

All percentages used herein are by weight of the composition unless otherwise indicated.

EXAMPLES

The following examples are made by conventional processes by mixing the following:

| Formulations of Examples 1–9 are at pH 7. % w/w of composition | | | | | | | | | |
|---|---|---|---|---|---|---|---|---|---|
| Ingredient | 1 | 2 | 3 | 4 | 5 | 6 | 7 | 8 | 9 |
| Sorbitol (70% soln) | 31.239 | 31.739 | 31.989 | 32.469 | 32.969 | 33.219 | 33.619 | 34.119 | 34.369 |
| USP Purified Water | 25.152 | 25.152 | 25.152 | 25.152 | 25.152 | 25.152 | 25.152 | 25.152 | 25.152 |
| Silica (precipitated) | 22.000 | 22.000 | 22.000 | 22.000 | 22.000 | 22.000 | 22.000 | 22.000 | 22.000 |
| Glycerin | 8.000 | 8.000 | 8.000 | 8.000 | 8.000 | 8.000 | 8.000 | 8.000 | 8.000 |
| Sodium Lauryl Sulfate Solution | 4.000 | 4.000 | 4.000 | 4.000 | 4.000 | 4.000 | 4.000 | 4.000 | 4.000 |
| Polyethylene glycol 300 | 1.000 | 1.000 | 1.000 | 1.000 | 1.000 | 1.000 | 1.000 | 1.000 | 1.000 |
| Sodium Fluoride, USP | 0.243 | 0.243 | 0.243 | 0.243 | 0.243 | 0.243 | 0.243 | 0.243 | 0.243 |
| Titanium Dioxide, Rutile | 0.525 | 0.525 | 0.525 | 0.525 | 0.525 | 0.525 | 0.525 | 0.525 | 0.525 |
| Xanthan Gum | 0.475 | 0.475 | 0.475 | 0.475 | 0.475 | 0.475 | 0.475 | 0.475 | 0.475 |
| Sodium Carboxymethylcellulose | 0.500 | 0.500 | 0.500 | 0.500 | 0.500 | 0.500 | 0.500 | 0.500 | 0.500 |
| Sodium Saccharin | 0.286 | 0.286 | 0.286 | 0.286 | 0.286 | 0.286 | 0.286 | 0.286 | 0.286 |
| Sodium Acid Pyrophosphate | 2.400 | 2.400 | 2.400 | 1.600 | 1.600 | 1.600 | 1.050 | 1.050 | 1.050 |
| Tetrasodium Pyrophosphate | 2.180 | 2.180 | 2.180 | 1.750 | 1.750 | 1.750 | 1.150 | 1.150 | 1.150 |
| Flavor | 1.000 | 1.000 | 1.000 | 1.000 | 1.000 | 1.000 | 1.000 | 1.000 | 1.000 |
| Casein Phosphopeptide-Amorphous Calcium Phosphate[1] | 1.000 | 0.500 | 0.250 | 1.000 | 0.500 | 0.250 | 1.000 | 0.500 | 0.250 |

[1] PP-ACP wherein the PP is derived from a tryptic digest of casein and having the sequence of T1, T2, T3, or T4 and ACP has the formula: $[Ca_3(PO_4)_{1.87}(HPO_4)_{0.2} \times H_2O]$ wherein $x \geq 1$.

The above fluoride levels represent levels (% by weight of composition) of fresh product. The formulations of Examples 1–9 are stored for either 30 days, 60 days, 90 days, 1 year, or 2 years (under either accelerated, e.g. at 40° C., or ambient conditions), and thereafter the levels of fluoride in the compositions are measured via one of the methods discussed supra. At the end of the storage interval, the levels of fluoride of the aged composition are no more than 20% less than the level of fluoride of fresh product.

What is claimed is:

1. A method of maintaining the fluoride levels in an oral care composition comprising a safe and effective amount of PP-ACP, a safe and effective amount of a fluoride ion source with free fluoride ions, and a pharmaceutically-acceptable topical, oral carrier, by adding, to the composition, from about 0.001% to about 20% of a calcium chelator;
   wherein the fluoride level for the aged composition is no more than about 20% lower than the level of fluoride in the fresh composition.

2. The method of claim 1 wherein the fluoride level for the aged composition is no more than about 15% lower than the level of fluoride in the fresh composition.

3. The method of claim 2 wherein the fluoride level for the aged composition is no more than about 10% lower than the level of fluoride in the fresh composition.

4. The method of claim 1 wherein the amount of PP-ACP is from about 0.1% to about 10% by weight of the composition.

5. The method of claim 4 wherein the level of PP-ACP is from about 0.2% to about 2% by weight of the composition.

6. The method of claim 5 wherein the calcium chelator is selected from the group consisting of tartaric acid and salts thereof, citric acid and salts thereof, pyrophosphate ion source, polyphosphate, diphosphonates, and mixtures thereof.

7. The method of claim 6 wherein the calcium chelator is selected from the group consisting of sodium citrate, potassium citrate, disodium tartrate, dipotassium tartrate, sodium potassium tartrate, disodium hydrogen tartrate, potassium hydrogen tartrate, pyrophosphate ion source, disodium dihydrogen pyrophosphate, tetrasodium pyrophosphate, tetrapotassium pyrophosphate, and mixtures thereof.

8. The method of claim 7 wherein the calcium chelator is a pyrophosphate ion source.

9. The method of claim 6 wherein the level of calcium chelator is from about 0.1% to about 5% by weight of the composition.

10. The method of claim 1 wherein the fluoride ion source provides free fluoride at a level of from about 850 ppm to about 1150 ppm of free fluoride ions.

11. The method of claim 1 wherein the PP-ACP contains the core sequence -Ser(P)-Ser(P)-Ser(P)-Glu-Glu-.

12. The method of claim 11 wherein PP includes the amino acid sequence selected from the group consisting of:

[1] $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}(59-79)$ ($T_1$);

[2] $Arg^1$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$ $\beta(1-25)$ ($T_2$);

[3] $Asn^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-$Lys^{70}$ $\alpha_{s2}(46-70)$ ($T_4$); and

[4] $Lys^1$-Asn-Thr-Met-Glu-His-Val-Ser(P)-Ser(P)-Ser(P)-Glu-Glu-Ser-Ile-Ile-Ser(P)-Gln-Glu-Thr-Tyr-$Lys^{21}$ $\alpha_{s2}(1-21)$ (T3).

13. The method of claim 1 wherein ACP is an amorphous form of calcium phosphate having the formula: $Ca_3(PO_4)_{1.87}(HPO_4)_{0.2} \cdot xH_2O$ where $x \geq 1$.

* * * * *